US006932785B1

(12) United States Patent
Shesol

(10) Patent No.: US 6,932,785 B1
(45) Date of Patent: Aug. 23, 2005

(54) ANATOMIC WOUND DRESSING HOLDER WITH AN INFINITELY ADJUSTABLE PRIMARY WOUND DRESSING

(76) Inventor: Barry F. Shesol, 18158 E. Long Ave., Aurora, CO (US) 80016

( * ) Notice: Subject to any disclaimer, the term of this patent is extended or adjusted under 35 U.S.C. 154(b) by 82 days.

(21) Appl. No.: 10/428,488

(22) Filed: May 3, 2003

(51) Int. Cl.$^7$ .............................................. A61F 13/00
(52) U.S. Cl. ...................................................... 602/79
(58) Field of Search .............................. 602/79, 67–69, 602/74, 75, 4, 19, 76, 77

(56) References Cited

U.S. PATENT DOCUMENTS 5,843,018 A * 12/1998 Shesol et al. .................. 602/79

* cited by examiner

Primary Examiner—Kim M. Lewis
(74) Attorney, Agent, or Firm—Edwin H. Crabtree; Ramon L. Pizarro; Donald W. Margolis

(57) ABSTRACT

An anatomic secondary wound dressing holder for providing painless access to a radiation wound and the like on the body of a patient. The secondary wound dressing holder is readily adaptable to various parts of the anatomy of the patient for holding one or more primary wound dressings on the wound of the patient. The secondary wound dressing holder includes an enlarged dressing holder portion with an outwardly extending first strap with a hook fastener thereon and a second strap. The hook fastener on the first strap is releasably attached to loose weave material along a length of the second strap, when the enlarged dressing holder portion is received on the patient. The invention also includes one or more primary wound dressings with hook fasteners thereon. The primary wound dressings are infinitely adjustable on the enlarged dressing holder portion for receipt on one or more wounds on the patient's upper and lower body.

16 Claims, 1 Drawing Sheet

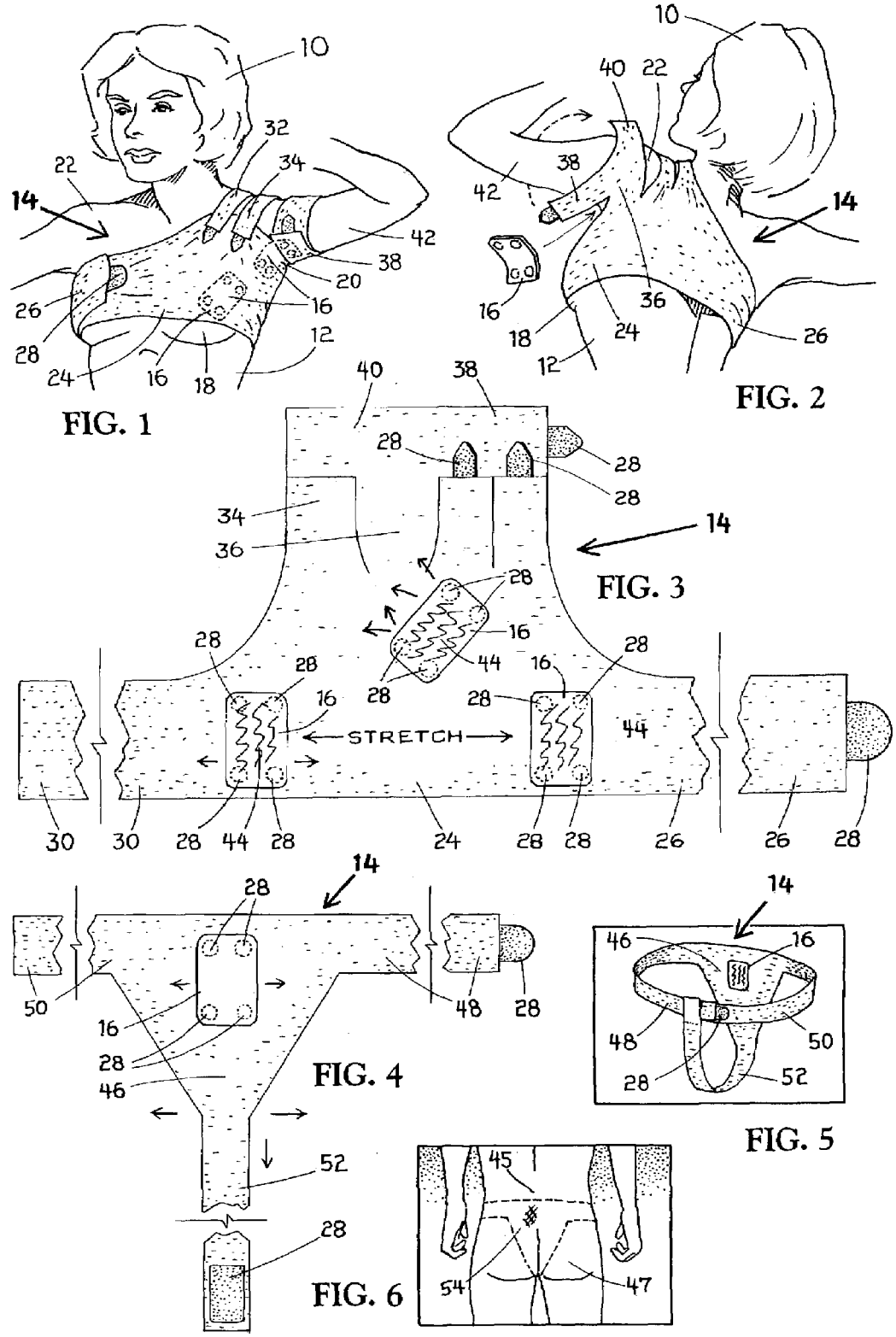

ANATOMIC WOUND DRESSING HOLDER WITH AN INFINITELY ADJUSTABLE PRIMARY WOUND DRESSING

BACKGROUND OF THE INVENTION (a) Field of the Invention

This invention relates to a wound dressing holder in combination with a primary wound dressing that has been modified for variable placement next to a wound and more particularly, but not by way of limitation, to a radiation therapy wound dressing holder anatomically designed with a converted primary wound dressing that may be held in place at any location over a radiation wound and the like for assisting in the healing of radiation therapy complications.

(b) Discussion of Prior Art

In the treatment of cancer by means of radiation therapy, serious wound problems are tolerated when compared to the primary problem of being treated by radiation. The radiation not only kills cancer cells, but by the very nature of it's action, healthy skin tissue, blood vessels, bone and other structures are inadvertently irreparably damaged. Each year almost one-half million new patients suffer some degree of radiation therapy damage. Therefore, it is of utmost value to have an anatomic wound dressing holder that would allow for the treatment of radiation burn complications without causing further or additional wound complications.

Heretofore, there have been a variety of different types of non-anatomic wound wraps used with adhesives, which in addition to the damage caused by the adhesive also cause some degree of pressure on the wound. Radiation therapy causes all tissues to have increased susceptibility to the inadvertent consequences caused by traditional wound retention. Therefore, the use of prior art wound wraps and the use of primary wound dressings with adhesives frequently result in an increase in the nature and severity of the original wound problems, while causing the already marginally viable tissue to further break down. The consequence is a dilemma to healthcare providers, who wish to deliver treatment to the wound in need of serious attention, but without causing further harm to the wound. The subject invention addresses this concern.

Furthermore, all previous wound dressing holders patented by the subject inventor consist of holders in which the location of the primary wound dressing is predetermined by the second wound dressing holder. This is manifested through the location of a window opening in the dressing holder, a transparent cover over the window opening or adhesive strips next to the window opening for holding the primary wound dressing next to the window opening.

In the subject invention, the location of the primary wound dressing is not limited by the predetermined components of the secondary dressing holder. Rather, the primary wound dressing is converted into a dressing that by the nature of it's modification of composition, is free to adhere anywhere on the secondary wound dressing holder. The secondary wound dressing holder has no predetermined limitations or restrictions for placement. Thus, the primary wound dressing is converted to a component that, with the unrestrictive secondary wound dressing holder, becomes one unit with infinite sites of application.

Another essential difference between the prior art wound dressing holders and the subject invention is the new secondary wound dressing holder provides for applications of a primary wound dressing at multiple wound sites. This is a function of no need for a predetermined window opening, window opening cover or adhesive strips on the sides of the window opening. Each primary wound dressing is converted to it's own unique component that forms a unit with the second wound dressing holder.

In U.S. Pat. Nos. 5,456,660, 5,662,599 and 6,258,051 to Shesol et al., a bidirectional disposable wound dressing and support unit is described for holding a variety of different size standard gauze pads on top of a wound and providing painless access to the wound without the use of adhesives. The disposable wound dressing and support unit is characterized by a window opening disposed along the length of the wrap. A gauze pad is releasably attached to the sides of the window opening. The window opening in the wrap allows for visual inspection of the gauze pad relative to the nature of wound drainage. This type of wound wrap, while effective in enhanced healing of a wound, is limited to the placement of the primary wound dressing next to the window opening or where an attachment has been provided during manufacture of the device. Also, this type of wound wrap does not lend itself to use on radiation wounds found in difficult and unaccessible areas of the body. Further, U.S. Pat. No. 6,258,051 discloses the wound wrap having adhesive strips along the length thereof for securing a sterile gauze pad thereto and without the use of a window opening. But, this wound wrap is not contoured for holding a primary wound dressing in certain large or small unaccessible anatomic areas of a patient's body. Also, the type of wound wrap has a predetermined wound dressing site. The adhesive strips on the secondary wound dressing holder do not allow for placement of the primary wound dressing other than next to strips.

The above mentioned prior art wound wraps do not provide the unique features, structure and function of the subject invention as described herein when addressing the need for a second wound dressing holder used in holding a primary wound dressing on wounds in difficult to treat anatomic areas of the body, where adjustment or repositioning of the primary wound dressing is required.

SUMMARY OF THE INVENTION

In view of the foregoing, it is a primary objective of the subject invention to provide a contoured anatomic secondary (radiation) wound dressing holder in combination with an adjustable primary wound dressing held in place next to a radiation wound on a patient's body. The second wound dressing holder can be painlessly secured, it is easily adjustable on the body and can be painlessly removed for replacing or adjusting the primary wound dressing attached thereto.

Another object of the wound dressing holder is to hold a primary wound dressing in certain large or small anatomic areas of the body having a recalcitrant wound. The wound dressing holder can be cut to allow for anatomic irregularities without fraying or loosing the holders functional integrity.

Yet another object of the wound dressing holder is to provide a primary wound dressing or dressings with hook attachments. The primary wound dressing with hook attachments can be releasably attached to loose weave material on an inside of the secondary wound dressing holder and at various selected locations thereon.

Still another object of the secondary wound dressing holder is to prevent movement of the primary wound dressing without the use of adhesives and with the desired tension to hold the wound dressing in place. The holder is lightweight, breathable, absorbable and latex free. Also, the wound dressing holder can be stretchable.

The subject invention broadly includes an anatomic secondary wound dressing holder for providing painless access to a radiation wound and the like on the body of a patient. The secondary wound dressing holder is readily adaptable to various parts of the anatomy of the patient for holding one or more primary wound dressings on the wound of the patient. The secondary wound dressing holder includes an enlarged dressing holder portion with an outwardly extending first strap with a hook fastener thereon and a second strap. The hook fastener on the first strap is releasably attached to loose weave material along a length of the second strap, when the enlarged dressing holder portion is received on the patient. The invention also includes one or more primary wound dressings with hook fasteners thereon. The primary wound dressings are infinitely adjustable on the enlarged dressing holder portion for receipt on one or more wounds.

These and other objects of the present invention will become apparent to those familiar with various types secondary wound dressing holders and primary wound dressing when reviewing the following detailed description, showing novel construction, combination, and elements as herein described, and more particularly defined by the claims, it being understood that changes in the embodiments to the disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which:

FIG. 1 is a front perspective view of a female patient with the subject secondary wound dressing holder holding a primary wound dressing over a radiation wound on her left breast and a primary wound dressing over a radiation wound on her left armpit.

FIG. 2 is a rear perspective view of the female patient showing the primary wound dressing being positioned for receipt under the left armpit and prior to securing the first and second arm straps.

FIG. 3 is a front view of the anatomic secondary wound dressing holder having chest straps, shoulder straps and arm straps for securing one or more primary wound dressing on the patient's upper body.

FIG. 4 is a front view of another embodiment of the anatomic secondary wound dressing holder used for holding a primary wound dressing in a perineal area of the patient's lower body.

FIG. 5. is a perspective view of the perineal wound dressing holder with a primary wound dressing attached to a portion of the holder.

FIG. 6. is a rear view of a patient having a radiation wound above the buttocks and prior to receiving the primary wound dressing and wound dressing holder thereon.

DETAILED DESCRIPTION OF THE PREFERRED EMBODIMENTS

In FIG. 1, a front perspective view of a female patient 10 is shown with the subject anatomic secondary wound dressing holder attached to her upper body 12. The secondary wound dressing holder is shown having general reference numeral 14. The secondary wound dressing holder 14 is used for holding in place one or more adjustable primary wound dressings 16 on the patient 10. In this example, the holder 14 is used to hold a primary wound dressing 16 over a radiation wound in her left breast 18 and a primary wound dressing 16 over a radiation wound on her left armpit 20. The primary wound dressings 16 are shown in dashed lines in this drawing.

In FIG. 2, a rear perspective view of the female patient 10 is illustrated with the primary wound dressing 16 being positioned for receipt under the left armpit 20 and prior to securing the wound dressing holder 14 to the patient's shoulder 22.

In FIG. 3, a front view of the inside of the anatomic secondary wound dressing holder 14 is shown. In this example, the wound dressing holder 14 includes an enlarged chest portion 24 for receipt over the patient's breasts. The chest portion 24 includes an outwardly extending first chest strap 26 with a hook fastener 28 thereon and a second chest strap 30. The hook fastener 28 on the first chest strap 26 is releasably attached to loose weave material at infinite positions along a length of the second chest strap 30, when the enlarged chest portion 24 is received on the patient's upper body 12. Obviously, the infinite adjustment of the hook fastener 28 on the second chest strap 30 allows for comfortably adjusting the holder 14 on the patient and holding one or more of the wound dressings 16 in place.

The wound dressing holder 14 can also include a first shoulder strap 32 with one or more hook fasteners 28 and a second shoulder strap 34. The two shoulder straps 32 and 34 are integrally attached to a top of the chest portion 24. In this example, two hook fasteners 28 are releasably attached to the loose weave material along a length of the second shoulder strap 34, as shown in FIG. 1.

Also, the wound dressing holder 14 can include an armpit or axilla portion 36 integrally attached to the top of the chest portion 24 and disposed between the first and second shoulder straps 32 and 34. The axilla portion 36 is used for holding the primary wound dressing 16 next to the armpit 20, as shown in FIGS. 1 and 2. It should be noted that by the nature of the contoured wound dressing holder 14, the axilla portion 36 is used in a small but difficult anatomic area of the body for holding the wound dressing 16 thereon. Obviously, the chest portion 24 is larger than the axilla portion 36 for holding one or more primary wound dressings 16 in the chest area of the patient. This important feature provides versatility to the anatomic secondary wound dressing holder 14, when compared to bidirectional wound wraps that are limited to holding a primary wound dressing on the limbs of the patient.

Also, a first arm strap 38 and a second arm strap 40 are attached to a top of the axilla portion 36. The first arm strap 38 includes a hook fastener 28 for releasable attachment the loose weave material along a length of the second arm strap 40, when the arm straps 38 and 40 are received around an upper arm 42 of the patient 10.

In this drawing, primary wound dressings 16 are shown with hook fasteners 28 for securing the dressing to a portion of the chest portion 24 for covering a radiation wound on both of the patient's breasts. Obviously, the primary wound dressing 16 with hook fasteners 28 can be placed and adjusted on infinite positions on the chest portion 24 using the loose weave material on the wound dressing holder 14. The primary wound dressings 16 can be various sizes of sterile gauze pads or similar radiation wound dressings. A gel or cream medication 44, shown as wavy lines, is placed on top of the dressing 16 for receipt on the wound. Also, shown in this drawing is a second wound dressing 16 positioned for attachment next to or on the axilla portion 36 of the holder 14. The primary wound dressings 16 with medication 44 obviously are placed over typical radiation wounds on the patient 10 that occur during the treatment of breast cancer and lymph gland cancer.

In FIG. 4, a front view of another embodiment of the anatomic secondary wound dressing holder 14 is shown and used for holding a primary wound dressing 16 in a perineal area of a patient's lower body 45. In this embodiment, the wound dressing holder 14 includes an enlarged buttocks portion 46 for receipt over a patient's buttocks 47. The lower body 45 and the buttocks 47 of the patient are shown in FIG. 6. The buttocks portion 46 includes an outwardly extending first waist strap 48 with a hook fastener 28 thereon and a second waist strap 50. The hook fastener 28 on the first waist strap 48 is releasably attached to loose weave material at infinite positions along a length of the second waist strap 50, when the enlarged buttocks portion 46 is received on the patient's buttocks 47.

Also, the wound dressing holder 14 includes a perineal strap 52 integrally attached to a bottom of the buttocks portion 46. The perineal strap 52 extends downwardly from the buttocks portion 46 and is perpendicular to the length of the waist straps 48 and 50 and is stretched at a right angle to the waist straps. An end of the perineal strap 52 includes a hook fastener 28 for releasable attachment to a portion of the first waist strap 48, as shown in FIG. 5.

In this drawing, a primary wound dressing 16 is shown with hook fasteners 28 releasably attached and adjustable on various locations on the buttocks portion 46. The primary wound dressing 16 is received over a radiation wound 54 above the patient's buttocks 47, as shown in FIG. 6.

In FIG. 5., a perspective view of the secondary wound dressing holder 14 is illustrated with the primary wound dressing 16 adjustably attached to a portion of the buttocks portion 46.

In FIG. 6., a rear view of the patient is shown having the radiation wound 54 disposed above the buttocks 47 and prior to receiving the primary wound dressing 16 and the secondary wound dressing holder 14 thereon. The position of the wound dressing holder 14 on the lower body 45 is shown in dashed lines.

It should be mentioned that while the hook fasteners 28 have been described above for securing the various straps on the secondary wound dressing holder 14 and the hook fasteners 28 securing the primary wound dressing 16 to the chest portion 24, the axilla portion 36 and the buttocks portion 46, other types of releasable fasteners can be used equally well without departing from the spirit and scope of the subject invention.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

What is claimed is:

1. A combination secondary wound dressing holder and primary wound dressing holder for receipt on a radiation wound and other types of wounds on a patient, the combination comprising:
   an enlarged wound dressing portion with an outwardly extending first strap with strap fastener means thereon and an outwardly extending second strap, said strap fastener means for releasable attachment along a length of said second strap when said enlarged wound dressing portion is received on the patient; and
   at least two primary wound dressings having wound dressing attachment means thereon for releasable attachment along a length and along a width of said enlarged wound dressing portion, said primary wound dressings providing direct contact on the wounds of the patient and without added medication on said primary wound dressings.

2. The combination as describe in claim 1 wherein said enlarged wound dressing portion is an enlarged wound dressing chest portion adapted for receipt on the patient's chest and said first and second straps are first and second chest straps for holding said enlarged wound dressing chest portion on the patient's chest.

3. The combination as described in claim 2 further including a first shoulder strap with shoulder strap fastener means thereon and a second shoulder strap, said first and second shoulder straps integrally attached to a top of said enlarged wound dressing chest portion, said shoulder strap fastener means for releasable attachment along a length of said second shoulder strap.

4. The combination as described in claim 3 further including an axilla portion integrally attached to the top of said enlarged wound dressing chest portion, said axilla portion having a first arm strap with arm strap fastener means thereon and a second arm strap, said arm strap fastener means for releasable attachment along a length of said second arm strap, said axilla portion for holding one of said primary wound dressings next to the patient's armpit.

5. The combination as described in claim 4 wherein said axilla portion is integrally attached to the top of said chest portion and disposed between said first and second shoulder straps.

6. The combination as described in claim 2 wherein said strap fastener means is a chest strap hook fastener, said chest strap hook fastener for releasable engagement of loose weave material along the length of said second chest strap and at infinite positions on said second chest strap.

7. The combination as described in claim 3 wherein said shoulder strap fastener means is a shoulder strap hook fastener, said shoulder strap hook fastener for releasable engagement of loose weave material along the length of said second shoulder strap and at infinite positions on said second shoulder strap.

8. The combination as described in claim 4 wherein said arm strap fastener means is an arm strap hook fastener, said arm strap hook fastener for releasable engagement of loose weave material along the length of said second arm strap and at infinite positions on said arm chest strap.

9. The combination as describe in claim 1 wherein said enlarged wound dressing portion is an enlarged buttocks portion with outwardly extending first waist strap with waist strap fastener means thereon and with an outwardly extending second waist strap, said waist strap fastener means for releasable attachment along a length of said second waist strap, when said enlarged buttocks portion is received on a patient's buttocks, said buttocks portion holding one of said primary wound dressings thereon.

10. The combination as described in claim 9 wherein said waist strap fastener means is a waist strap hook fastener, said waist strap hook fastener for releasable engagement of loose weave material along the length of said second waist strap and on said second waist strap.

11. A combination secondary wound dressing holder and primary wound dressing for receipt on a radiation wound and other types of wounds on an upper body of a patient, the combination comprising:

an enlarged chest portion with an outwardly extending first chest strap with a chest strap hook fastener thereon and an outwardly extending second chest strap, said chest strap hook fastener for releasable attachment to loose weave material along a length of said second chest strap when said enlarged chest portion is received on the patient's chest;

a first shoulder strap with a shoulder strap hook fastener thereon and a second shoulder strap, said first and second shoulder straps integrally attached to a top of said chest portion, said shoulder strap hook fastener for releasable attachment to loose weave material along a length of said second shoulder strap;

an axilla portion integrally attached to the top of said chest portion, said axilla portion having a first arm strap with an arm strap hook fastener thereon and a second arm strap, said arm strap hook fastener for releasable attachment to loose weave material along a length of said second arm strap, said axilla portion adapted for holding a primary wound dressing next to the patient's armpit, and at least one primary wound dressing with wound dressing attachment means, said wound dressing attachment means for releasable attachment on said enlarged chest portion and said axilla portion.

12. The wound dressing holder as described in claim 11 wherein said axilla portion is integrally attached to the top of said chest portion and disposed between said first and second shoulder straps.

13. A combination secondary wound dressing holder and primary wound dressing for receipt on a radiation wound and other types of wounds on a lower body of a patient, the combination comprising:

an enlarged buttocks portion with an outwardly extending first waist strap with waist chest strap fastener means thereon and with an outwardly extending second waist strap, said waist strap fastener means for releasable attachment to loose weave material along a length of said second waist strap, when said enlarged buttocks portion is received on a patient's buttocks;

a perineal strap with perineal fastener means thereon, said perineal strap integrally attached to a bottom of said buttocks portion and disposed at a right angle to said first and second waist straps, said perineal fastener means for releasable attachment to loose weave material along a length of said first waist strap; and at least one primary wound dressing with wound dressing attachment means thereon, said wound dressing attachment means for releasable attachment at infinite on said enlarged buttocks portion.

14. The wound dressing holder as described in claim 13 wherein said waist strap fastener means is a waist strap hook fastener, said waist strap hook fastener for releasable engagement to loose weave material along the length of said second waist strap.

15. The wound dressing holder as described in claim 13 wherein said perineal strap fastener means is a perineal strap hook fastener, said perineal strap hook fastener for releasable engagement of the loose weave material along the length of said first waist strap.

16. The wound dressing holder as described in claim 13 wherein said wound dressing attachment means is a plurality of wound dressing hook fasteners, said wound dressing hook fasteners for securing said primary wound dressing to loose weave material on said enlarged buttocks portion.

* * * * *